United States Patent [19]

Glenn

[11] Patent Number: 5,028,731
[45] Date of Patent: Jul. 2, 1991

[54] PREPARATION OF MIXTURES OF CYPERMETHRIN OR CYFLUTHRIN ISOMERS ENRICHED IN MORE ACTIVE SPECIES

[75] Inventor: Michael S. Glenn, Langhorne, Pa.

[73] Assignee: FMC Corporation, Philadelphia, Pa.

[21] Appl. No.: 438,657

[22] Filed: Nov. 17, 1989

[51] Int. Cl.$^5$ .......................................... C07C 253/30
[52] U.S. Cl. .................................................... 558/407
[58] Field of Search ........................................ 558/407

[56] References Cited

U.S. PATENT DOCUMENTS

| | | | |
|---|---|---|---|
| 2,769,835 | 11/1956 | Kosmin et al. | 560/213 |
| 3,078,306 | 2/1963 | von Schickh et al. | 560/250 |
| 3,082,236 | 3/1963 | Mageli et al. | 558/263 |
| 4,024,163 | 5/1977 | Elliott et al. | 558/407 X |
| 4,536,345 | 8/1985 | Martel et al. | 558/407 |

FOREIGN PATENT DOCUMENTS 60-202843 3/1984 Japan .

OTHER PUBLICATIONS

Weygand/Hilgetag, "Preparation Organic Chemistry", (1972), p. 378, John Wiley & Sons, N.Y., Sydney, London, Toronto.

Primary Examiner—Joseph Paul Brust
Attorney, Agent, or Firm—H. Robinson Ertelt; Robert M. Kennedy

[57] ABSTRACT

A mixture of isomers of cypermethrin or cyfluthrin enriched in the more insecticidally active $c_2$ or $t_2$ isomer, or both, is prepared by adding α-hydroxy-3-phenoxyphenylacetonitrile or its 4-fluoro analog to a refluxing solution of 3-(2,2-dichloroethenyl)-2-2-dimethylcyclopropanecarbonyl chloride in a hydrocarbon solvent boiling in the range of about 75° to 115° C. in an inert atmosphers, without an acid acceptor being present in the reaction mixture. The product is recovered by washing the reaction mixture with aqueous base.

7 Claims, No Drawings

PREPARATION OF MIXTURES OF CYPERMETHRIN OR CYFLUTHRIN ISOMERS ENRICHED IN MORE ACTIVE SPECIES

TECHNICAL FIELD

This invention relates to an improvement in a chemical process. In particular, it relates to an improved esterification process that results in enantiomerically enriched (R,S)-(cyano)(3-phenoxyphenyl)-methyl cis/-trans-3-(2,2-dichloroethenyl)-2,2-dimethylcyclopropanecarboxylate (cypermethrin) or (R,S)-(cyano)(4-fluoro-3-phenoxyphenyl)methyl cis/trans-3-(2,2-dichloroethenyl)-2,2-dimethylcyclopropanecarboxylate (cyfluthrin). It also relates to the preparation of similarly enriched mixtures of diastereomers. This process improvement requires the esterification of a substituted-cyclopropanecarbonyl chloride with an appropriate cyanohydrin without an acid acceptor being present. The product ester is enriched in the more insecticidally active enantiomers or diastereomers compared to the product produced by the same reaction with an acid acceptor present.

BACKGROUND OF THE INVENTION

Both cypermethrin (U.S. Pat. No. 4,024,163) and cyfluthrin (U.S. Pat. No. 4,218,469) are well-known pyrethroid insecticides and are articles of commerce in many countries. Each may contain eight isomers.

For racemic cypermethrin the eight isomers are designated I-VIII as follows:

```
              cis isomers
  I   =  (S)-(cyano)(3-phenoxyphenyl)methyl 1R,cis-3-(2,2-di-
         chloroethenyl)-2,2-dimethylcyclopropanecarboxylate
         (abbreviated 1R,cis S)
  II  =  (R)-(cyano)(3-phenoxyphenyl)methyl 1S,cis-3-(2,2-di-
         chloroethenyl)-2,2-dimethylcyclopropanecarboxylate
         (abbreviated 1S,cis R)
  III =  (S)-(cyano)(3-phenoxyphenyl)methyl 1S,cis-3-(2,2-di-
         chloroethenyl)-2,2-dimethylcyclopropanecarboxylate
         (abbreviated 1S,cis S)
  IV  =  (R)-(cyano)(3-phenoxyphenyl)methyl 1R,cis-3-(2,2-di-
         chloroethenyl)-2,2-dimethylcyclopropanecarboxylate
         (abbreviated 1R,cis R)
              trans isomers
  V   =  (1R,trans S), the trans isomer of I
  VI  =  (1S,trans R), the trans isomer of II
  VII =  (1S,trans S), the trans isomer of III
  VIII=  (1R,trans R), the trans isomer of IV
```

The designations 1R,cis; 1R,trans; 1S,cis: and 1S,trans refer to the spatial relationship of the hydrogen atoms at the 1 and 3 positions of the cyclopropane ring, and the single letter designations R and S refer to the spatial configuration of the cyano group on the alpha carbon of the alcohol portion of the molecule.

The same designations are applied to the corresponding isomers of cyfluthrin.

It is well known that the most insecticidally active isomers are I and V. It is also well known that the enantiomer pairs I/II, referred to as the $c_2$ enantiomer pair, and V/VI, referred to as the $t_2$ enantiomer pair, are more insecticidally active than the enantiomer pairs, III/IV, referred to as the $c_1$ enantiomer pair, and VII/-VIII, referred to as the $t_1$ enantiomer pair.

It is extremely difficult and commercially impractical to separate the more active isomers from the complex mixture of isomers produced in the usual synthesis of pyrethroids. Consequently, substantial effort has been devoted to methods for increasing the proportion of active isomers in products consisting of mixtures of isomers, e.g., by converting less active isomers in such mixtures to more active isomers. Such processes are disclosed in U.S. Pat. Nos. 4,427,598 and 4,782,174, inter alia.

While the increased processing costs incurred in such isomer enrichment techniques may be justified for some pesticidal applications, an esterification process which would lead directly to a mixture enriched in the more active isomers would be highly desirable, both for the increased insecticidal activity of the esterification product itself and as an enhanced feed stock for conversion.

SUMMARY OF THE INVENTION

It has now been found that the reaction of an α-hydroxyphenoxyphenylacetonitrile with a solution of the appropriate cyclopropanecarbonyl chloride in the absence of an acid acceptor gives a product enriched in the more active isomers over the product obtained when an acid acceptor is present. The conventional process for reacting an acid chloride with an alcohol calls for the presence of a stoichiometric amount of an acid acceptor, usually pyridine or another tertiary amine, to react with the hydrogen chloride liberated in the reaction.

More recently Japanese Kokai 60-202843, (Sumitomo Chemical Industries KK), has described a process for preparing esters, including pyrethroid esters, from acid halides and alcohols while omitting the acid acceptor. This is accomplished either by running the reaction under reduced pressure to draw off the hydrogen halide gas or by sparging the reaction mixture with an inert gas, nitrogen or helium, and removing the hydrogen halide by entrainment in the gas stream. Example 9 of the Kokai makes (S)-α-cyano-3-phenoxybenzyl (1R,cis)-2,2-dimethyl-3-(2,2-dibromovinyl)cyclopropane-1-carboxylate from (S)-α-hydroxy-3-phenoxyphenylacetonitrile. Although this reference teaches the esterification in the absence of an acid acceptor, it does not and could not teach the advantageous effect on the $c_1/c_2$ or $t_1/t_2$ ratio of applying this process to cypermethrin or cyfluthrin mixtures, since only one isomer was produced.

Also, while the Kokai prefers either a vacuum of 500 mm of mercury or less or a inert gas flow in excess of 5 times the volume of hydrogen chloride liberated in the reaction, the present process requires only that the process be carried out under an inert gas. The most practical approach is to have a gentle flow of inert gas carrying the hydrogen chloride to a scrubber (to avoid the pollution that would be caused by venting the hydrogen chloride to the atmosphere), but as will be shown, the beneficial effect on isomer ratios is obtained even if the reaction is run in a vessel simply flushed with an inert gas.

DETAILED DESCRIPTION

In the process of this invention essentially equimolar amounts of α-hydroxy-3-phenoxyphenylacetonitrile (or its 4-fluoro analog) and cis/trans-3-(2,2-dichloroethenyl)-2,2-dimethylcyclopropanecarbonyl chloride are reacted in a hydrocarbon solvent at reflux without an acid acceptor being present. In the preparation of cypermethrin this process typically produces product having $c_1/c_2$ and $t_1/t_2$ isomer ratios of 48/52. The nearly identical process utilizing the same reactants in the presence of an acid acceptor, e.g., pyridine, yields cypermethrin typically having $c_1/c_2$ and $t_1/t_2$ ratios of 55/45. Thus, the amounts of $c_2$ and $t_2$ enantiomer pairs are increased relative to the $c_1$ and $t_1$ pairs, resulting in cypermethrin having correspondingly increased insecticidal activity.

It will be noted that the reactions with and without acid acceptor are run at different temperatures. The reason for this is that when pyridine is present the reaction must be run at lower temperatures, since at high temperatures the pyridine attacks the cyanohydrin, causing a reduction in yield. When pyridine is absent, the reaction must be run at higher temperatures, preferably reflux for the preferred mixed heptanes solvent, to drive off the hydrogen chloride produced. Thus a comparison at the same temperature would not be meaningful.

The only process variable that appears to be at all critical is the temperature of the reaction, which should be high enough to drive off the hydrogen chloride formed, but not high enough to degrade either the reactants or the product. Temperature is preferably controlled by choosing a solvent that refluxes in the range of about 75 to 115° C. The nature of the hydrocarbon solvent appears not to be critical, both aromatic and aliphatic solvents having been used effectively. Neither is reaction time critical, within limits that will be readily apparent to the chemist. The rate of chloride must be such that the reaction does not get out of control, and the completion of the reaction can be followed by cessation of the evolution of hydrogen chloride.

The following Examples are given to further illustrate the process of the invention.

EXAMPLE 1

Prior Art Process

Preparation of
(R,S)-(Cyano)(3-Phenoxyphenyl)Methyl
Cis/Trans-3-(2,2-Dichloroethenyl)-2,2-Dimethylcyclopropanecarboxylate in the Present of Pyridine as an Acid Acceptor In a stirred flask under nitrogen were placed 61.1 g (0.252 mole) of (R,S)-α-cyano-3-phenoxyphenylacetonitrile (93% purity), 22.3 g (0.280 mole) of pyridine, and 500 ml of toluene. While the temperature of the reaction was held between 35° C. and 43° C., a solution of 61.6 g (0.253 mole) of 3-(2,2-dichloroethenyl)-2,2-dimethylcyclopropanecarbonyl chloride (93.7% purity) in 50 ml of toluene was added dropwise over a period of 100 minutes. The reaction mixture was stirred for two hours, and then an additional 1.89 g (0.008 mole) of 3-(2,2-dichloroethenyl)-2,2-dimethylcyclopropanecarbonyl chloride (93% purity) was added. The reaction mixture was stirred for an additional 138 minutes before 75 ml of water was added to quench the reaction. The aqueous phase was separated and discarded, and the organic phase was washed in succession with 75 ml portions of 2N hydrochloric acid, a 10% solution of sodium carbonate in water, and pure water. After separation of the final wash, the solvent was removed from the organic phase under reduced pressure, leaving a liquid residue weighing 109.0 g. Analysis of this residue by liquid chromatography showed that 89.3% was (R,S)-(cyano)(3-phenoxyphenyl)methyl cis/trans-3-(2,2-dichloroethenyl)-2,2-dimethylcyclopropanecarboxylate. The cis/trans composition was 48.8/51.2, and the $c_1/c_2$ and $t_1/t_2$ 56.7/43.3, respectively. The yield of product was 92.8%, based on the amount of α-hydroxy-3-phenoxyphenylacetonitrile used in the reaction.

EXAMPLE 2

Preparation of
(R,S)-(Cyano)(3-Phenoxyphenyl)Methyl
CIS/Trans-3-(2,2-Dichloroethenyl)-2,2-Dimethyl-Cyclopropanecarboxylate Without an Acid Acceptor Present In a stirred flask were placed 733.2 g (1.505 moles) of a solution containing 46.7% of cis/trans-3-(2,2-dichloroethenyl)-2,2-dimethylcyclopropanecarbonyl chloride and 175 ml of mixed heptanes. A nitrogen atmosphere was maintained over the solution, which was heated to reflux. Dropwise, 354.1 g (1.462 moles) of (R,S(-α-hydroxy-3-phenoxyphenylacetonitrile (93% purity) was added to the refluxing solution over a 104 minute period. When the addition was complete, the reaction mixture was heated at reflux for one hour, then cooled and quenched with 375 ml of a 10% solution of sodium carbonate in water. After stirring for thirty minutes, the aqueous phase was separated from the organic reaction mixture and the organic phase was washed with 375 ml of water. Following separation from the aqueous wash, the solvent was removed from the organic phase under reduced pressure. A liquid residue weighing 631.1 g remained. Analysis of this residue by liquid chromatography showed that 92.4% of its composition was (R,S)-(cyano)(3-phenoxyphenyl)methyl cis/trans-3-(2,2-dichloroethenyl)-2,2-dimethylcyclopropanecarboxylate. The cis/trans composition was 53.2/46.8, and the $c_1/c_2$ and $t_1/t_2$ enantiomer pair compositions were 48.2/51.8 and 47.9/52.1, respectively. The yield of product was 95.8%, based on the amount of α-hydroxy-3-phenoxyphenylacetonitrile used in the reaction.

EXAMPLE 3

Preparation of
(R,S)-(Cyano)(3-Phenoxyphenyl)Methyl
Cis/Trans-3-(2,2-Dichloroethenyl)-2,2-Dimethylcyclopropanecarboxylate Without an Acid Acceptor Present and With an Argon Sparge In a flask were placed 68.1 g (0.200 mole) of cis/trans-3-(2,2-dichloroethenyl)-2,2-dimethylcyclopropanecarbonyl chloride (66.8% purity) and 100 mL of heptanes. An argon sparge was placed below the surface of the liquid, and a flow of argon was maintained throughout the reaction period. The reaction mixture was heated to reflux, and 49.2 g (0.203 mole) of R,S-α-hydroxy-3-phenoxyphenylacetonitrile (93% purity) was added dropwise over a 110 minute period. Heating at reflux was continued for an additional hour after completion of addition. The temperature of the reaction mixture was reduced to 60° C., and 55 mL of a 10% aqueous solution of sodium carbonate was added to it. The mixture was stirred vigorously for 30 minutes, after which the aqueous phase was separated and discarded. Distilled water was then added to the reaction mixture, and this mixture was then stirred at 50° C. for 30 minutes. The phases were separated, and the solvent for the organic phase was evaporated under reduced pressure, leaving a residue weighing 87.2 g. Analysis of this residue by liquid chromatography revealed that 90.5% of its composition was (R,S)-(cyano)(3-phenoxyphenyl)-methyl cis/trans-3-(2,2-dichloroethenyl)-2,2-dimethylcyclopropanecarboxylate. The cis/trans composition of this product was 51.4/48.6, and the $c_1/c_2$ and $t_1/t_2$ enantiomer pair compositions were 48.6/51.4 and 48.4/51.6, respectively. The yield of product was 94.8%, based on the amount of cis/trans-3-(2,2-dichloroethenyl)-2,2-dimethylcyclopropanecarbonyl chloride used in the reaction.

EXAMPLE 4

Preparation of (R,S)-(Cyano)(3-Phenoxyphenyl)Methyl Cis/Trans-3-(2,2-Dichloroethenyl)-2,2-Dimethylcyclopropanecarboxylate Without an Acid Acceptor Present and Without Inert Gas Flow A flask was flushed with nitrogen before 170.2 g (0.500 mole) of cis/trans-3-(2,2-dichloroethenyl)-2,2-dimethylcyclopropanecarbonyl chloride (66.8% purity) and 185 ml of heptanes were placed in it. No additional nitrogen was introduced into the reaction mixture after heating of the flask commenced. The reaction mixture was stirred vigorously. After vigorous reflux was established, 122.0 g (0.504 mole) of (R,S)-α-cyano-3-phenoxyphenylacetonitrile (93% purity) was added dropwise to the reaction mixture during a 130 minute period. Upon completion of addition, heating was continued for an additional 70 minutes after which the reaction mixture was cooled to 75° C., and 125 mL of a 10% aqueous solution of sodium carbonate was added. This mixture was stirred at 45-50° C. for 30 minutes after which the aqueous phase was separated and discarded. Distilled water (125 mL) was added to the reaction mixture, and the mixture was stirred at 45-50° C. for 30 minutes. The phases were then separated and the solvent removed from the organic phase under reduced pressure, leaving a residue weighing 215.1 g. Analysis of this residue by liquid chromatography revealed that 92.5% of its composition was (R,S)-(cyano)(3-phenoxyphenyl)methyl cis/trans-3-(2,2-dichloroethenyl)-2,2-dimethylcyclopropanecarboxylate. The cis/trans composition of this produce was 51.8/48.2, and the $c_1/c_2$ and $t_1/t_2$ enantiomer pair compositions were 48.9/51.1 and 47.8/52.2, respectively. The yield of product was 95.6% based on the amount of cis/trans-3-(2,2-dichloroethenyl)-2,2-dimethylcyclopropanecarbonyl chloride used in the reaction.

The foregoing Examples have all produced eight isomer mixtures of cypermethrin. The process is equally applicable to reactions in which the acid chloride is predominantly cis or predominantly trans and to the production of enhanced isomer mixtures of cyfluthrin. Table 1 shows typical reactions of cis-(>90% cis), cis/trans-, or trans-3-(2,2-dichloroethenyl)-2,2-dimethylcyclopropanecarbonyl chloride (>90% trans) with racemic or (S)-α-hydroxy-3-phenoxyphenylacetonitrile or racemic α-hydroxy-(4-fluoro-3-phenoxyphenyl)acetonitrile. In all cases the cis/trans ratio of the starting material is preserved in the ester product; only the $c_1/c_2$ and $t_1/t_2$ ratios are altered. Yields of 93–97% are usually obtained and do not reflect any dependency on one reactant or the other being present in a slight excess. In all cases the reactions were carried out under inert gas, either argon or nitrogen, usually with a slight flow of gas over the surface of the reaction mixture, less frequently with sparging. There is no indication that the manner of maintaining an inert atmosphere in the reaction vessel is in the least critical.

TABLE I

| Ex. | DVAC[a] (moles) | Cyanohydrin[b] (moles) | Solvent Type | Solvent Amount (ml) | Temp. (°C.) | Time Addition (min) | Time Heating (min) | Product Weight (g) | Pyrethroid (%) | Yield[c] (%) | Product Analysis cis/trans[d] | $c_1/c_2$[e] | $t_1/t_2$[f] |
|---|---|---|---|---|---|---|---|---|---|---|---|---|---|
| 5 | 0.503 | 0.501 | heptanes | 245 | 102–105 | 90 | 45 | 212.1 | 93.3 | 94.9 | 51.3/48.7 | 48.1/51.9 | 48.2/51.8 |
| 6 | 0.200 | 0.205 | heptanes/toluene | 100/10 | 100–101 | 75 | 60 | 87.1 | 90.8 | 95.0 | 5.4/95.6 | 47.7/52.3 | 48.3/51.7 |
| 7 | 0.093 | 0.090 | heptanes | 45 | 100–101 | 90 | 60 | 35.9 | 91.7 | 87.9 | 4.9/95.1 | 49.7/50.3 | 49.4/50.6 |
| 8 | 0.200 | 0.204 | " | 75 | 100–102 | 85 | 75 | 89.1 | 90.5 | 96.8 | 51.1/48.9 | 48.2/51.8 | 48.3/51.7 |
| 9 | 0.500 | 0.504 | " | 185 | 98–102 | 110 | 0 | 213.4 | 92.1 | 94.4 | 51.5/48.5 | 48.3/51.7 | 47.9/52.1 |
| 10 | 0.500 | 0.503 | " | 185 | 101–102 | 115 | 30 | 216.4 | 90.3 | 93.9 | 51.5/48.5 | 48.5/51.5 | 47.7/52.3 |
| 11 | 3.534 | 3.506 | " | 820 | 95–97 | 139 | 44 | 1494.4 | 92.8 | 95.0 | 52.1/47.9 | 48.2/51.8 | 48.3/51.7 |
| 12 | 0.452 | 0.434 | heptanes | 235 | 108–110 | 360 | 0 | 186.9 | 91.2 | 94.3 | 95.9/4.1 | 47.7/52.3 | 48.6/51.4 |
| 13 | 0.506 | 0.505[h] | toluene | 100 | 109–111 | 140 | 60 | 235.0 | 86.7 | 96.9 | 52.3/47.7 | 47.4/52.6 | 47.5/52.5 |
| 14 | 0.505 | 0.500[h] | heptanes | 120 | 100–104 | 96 | 98 | 213.9 | 96.8 | 99.5 | 50.4/49.6 | 49.0/51.0 | 48.7/51.3 |
| 15 | 0.505 | 0.482[h] | heptanes | 245 | 99–102 | 125 | 60 | 215.9 | 88.8 | 95.5 | 52.5/47.5 | 49.3/50.7 | 48.8/51.2 |
| 16 | 0.250[g] | 0.250[h] | toluene | 550 | 40–45 | 75 | 120 | 113.6 | 87.3 | 95.3 | 49.5/50.5 | 52.2/47.8 | 52.0/48.0 |
| 17 | 0.200 | 0.206[h] | heptanes | 45 | 101–104 | 110 | 134 | 89.8 | 84.8 | 91.5 | 98.7/1.3 | 49.0/51.0 | 46.2/53.8 |
| 18 | 0.250 | 0.289[i] | heptanes | 30 | 101–105 | 107 | 60 | 125.6 | 81.3 | 94.1 | 53.5/46.5 | 47.7/52.3 | 48.0/52.0 |
| 19 | 0.275[g] | 0.289[i] | toluene | 550 | 36–37 | 90 | 183 | 132.2 | 78.8 | 87.3 | 55.4/44.6 | 54.6/45.4 | 54.8/45.2 |

Footnotes to Table of Experiments
[a]3-(2,2-dichloroethenyl)-2,2-dimethylcyclopropylcarbonyl chloride
[b]α-Hydroxy-3-phenoxyphenylacetonitrile
[c]Based on the reactant (DVAC or cyanohydrin) introduced into the reaction in smaller molar amount.
[d]Ratio of cis- and trans-cyclopropyl moieties present.
[e]$c_1$ = 1S,cis S and 1R,cis R enantiomer pair of isomers
$c_2$ - 1R,cis S and 1S,cis R enantiomer pair of isomers
[f]$t_1$ = 1S,trans S and 1R,trans R enantiomer pair of isomers
$t_2$ = 1R,trans S and 1S,trans R enantiomer pair of isomers
[g]More than 1 molar equivalent of pyridine present during the reaction to serve as an acid acceptor.
[h](S)-α-hydroxy-3-phenoxyphenylacetonitrile
$c_1$ = 1S,cis S
$c_2$ - 1R,cis S
$t_1$ = 1S,trans S
$t_2$ = 1R,trans S
[i]α-hydroxy-4-fluoro-3-phenoxyphenylacetonitrile While the change from about 56/44 $c_1/c_2$ and $t_1/t_2$ may seem relatively modest, the resulting increase in insecticidal activity is consistent, providing a more effective product without the high cost of sophisticated separation techniques. This increase in activity is illustrated in Table II in which the test insect is the economically important tobacco budworm.

TABLE II

| | Foliar $LC_{50}$ (ppm) - Tobacco Budworm | |
|---|---|---|
| | Acid Acceptor (Example 1) | No Acid Acceptor (Example 5) |
| $c_1/c_2$:$t_1/t_2$ | 55.9/44.1:56.7/43.3 | 48.1/51.9:48.2/51.8 |
| Test 1 | 8.4 | 6.5 |
| Test 2 | 18.7 | 12.3 |
| Test 3 | 12.5 | 11.0 |
| Average | 13.2 | 9.9 |

I claim:

1. In the process for the preparation of a mixture of isomers of cypermethrin or cyfluthrin by reacting α-hydroxy-3-phenoxyphenylacetonitrile or its 4-fluoro analog with a solution of 3-(2,2-dichloroethenyl)-2,2-dimethylcyclopropanecarbonyl chloride, the improvement that comprises increasing the concentration of the $c_2$ or $t_2$ isomers or both relative to the $c_1$ or $t_1$ isomers by carrying out the reaction at atmospheric pressure in an inert atmosphere by adding, at a rate such that the reaction does not get out of control, the acetonitrile to a refluxing solution of the acid chloride in a hydrocarbon solvent boiling in the range of about 75 to 115° C., no acid acceptor being present in the reaction mixture, washing the reaction mixture with aqueous base, and recovering the product.

2. The process of claim 1 in which the α-hydroxy-3-phenoxyphenylacetonitrile has the R,S configuration and the acid chloride has the R,S-cis/trans configuration.

3. The process of claim 1 in which the α-hydroxy-3-phenoxyphenylacetonitrile has the R,S configuration and the acid chloride has the R,S-cis configuration.

4. The process of claim 1 in which the α-hydroxy-3-phenoxyphenylacetonitrile has the R,S configuration and the acid chloride has the R,S-trans configuration.

5. The process of claim 1 in which the α-hydroxy-3-phenoxyphenylacetonitrile has the S configuration and the acid chloride has the R,S-cis/trans configuration.

6. The process of claim 1 in which the α-hydroxy-3-phenoxyphenylacetonitrile has the S configuration and the acid chloride has the R,S-cis configuration.

7. The process of claim 1 in which the α-hydroxy-3-phenoxyphenylacetonitrile has the S configuration and the acid chloride has the R,S-trans configuration.

* * * * *

UNITED STATES PATENT AND TRADEMARK OFFICE
CERTIFICATE OF CORRECTION

PATENT NO. : 5,028,731
DATED : July 2, 1991
INVENTOR(S) : Michael S. Glenn

It is certified that error appears in the above-identified patent and that said Letters Patent is hereby corrected as shown below:

Column 3, line 28, "The rate of chloride" should read --The rate of addition of cyanohydrin to refluxing solution of acid chloride--.

Column 3, line 40, "in the Present of Pyridine" should read --in the Presence of Pyridine--.

Col. 6, lines 18-19, "α-hydroxy-(4-fluoro-3-phenoxyphenyl-)acetonitrile." should read --α-hydroxy-(4-fluoro-3-phenoxyphenyl)-acetonitrile--.

Signed and Sealed this

Twenty-second Day of December, 1992

Attest:

DOUGLAS B. COMER

Attesting Officer

Acting Commissioner of Patents and Trademarks